US006509195B1

(12) United States Patent
De Rooij et al.

(10) Patent No.: US 6,509,195 B1
(45) Date of Patent: Jan. 21, 2003

(54) ELECTROCHEMOLUMINESCENT DETECTOR

(75) Inventors: Nico De Rooij, Bôle (CH); Giovanni C. Fiaccabrino, Onnens (CH); Milena Koudelka-Hep, Neuchâtel (CH)

(73) Assignee: CSEM Centre Suisse d'Electronique et de Microtechnique SA, Neuchatel (CH)

( * ) Notice: Subject to any disclaimer, the term of this patent is extended or adjusted under 35 U.S.C. 154(b) by 0 days.

(21) Appl. No.: 09/445,663
(22) PCT Filed: Jun. 8, 1998
(86) PCT No.: PCT/CH98/00246
§ 371 (c)(1), (2), (4) Date: Mar. 2, 2000
(87) PCT Pub. No.: WO98/57154
PCT Pub. Date: Dec. 17, 1998

(30) Foreign Application Priority Data

Jun. 9, 1997 (FR) ............................................ 97 07269

(51) Int. Cl.$^7$ ............................................. G01N 21/76
(52) U.S. Cl. ...................... 436/172; 422/52; 250/361 C
(58) Field of Search ................................ 422/52, 82.01; 250/361 C; 436/172

(56) References Cited

U.S. PATENT DOCUMENTS

| | | | |
|---|---|---|---|
| 5,093,268 A | * | 3/1992 | Leventis et al. ............ 436/172 |
| 5,439,647 A | * | 8/1995 | Saini ........................ 422/82.11 |
| 5,744,367 A | * | 4/1998 | Talley et al. ................. 436/172 |
| 6,140,045 A | * | 10/2000 | Wohlstadter et al. .......... 435/6 |
| 6,200,531 B1 | * | 3/2001 | Liljestrand et al. ........... 422/52 |

OTHER PUBLICATIONS

Fiaccabrino, G.C. et al On Chip Detection of Electrogenerated Chemiluminescence of Ru(pby) at Pt Interdigitated Microelectrode Arrays, Transducers, pp. 171–174 (Jun. 16–19, 1997).*

Smith, R.L. "Electrochemiluminescence at microelectrodes for biosensing" SPIE vol. 2978, pp. 64–68 (Feb. 10–11, 1997).*

* cited by examiner

Primary Examiner—Jeffrey Snay
(74) Attorney, Agent, or Firm—Baker Botts L.L.P.

(57) ABSTRACT

Electrochemoluminescent detector for analyzing a biochemical or biological substance, comprising at least a cell (11, 12) generating and detecting the electrogenerated chemoluminescence, which includes: at least a working electrode (16, 17) produced on a substrate (20); electric power supply (13) connected to the electrode; a photodiode (14) detecting the light generated by electrochemoluminescence; and a device for measuring the signal delivered by the photodiode. The photodiode (14) is produced by being integrated in the substrate (20). The cell comprises two interdigital working electrodes protected by a passivation layer (18) leaving part of their top surface in contact with outside. An intermediate layer (19) of dielectric material is inserted between the electrodes and the substrate (20).

20 Claims, 2 Drawing Sheets

ELECTROCHEMOLUMINESCENT DETECTOR

Figure 1:
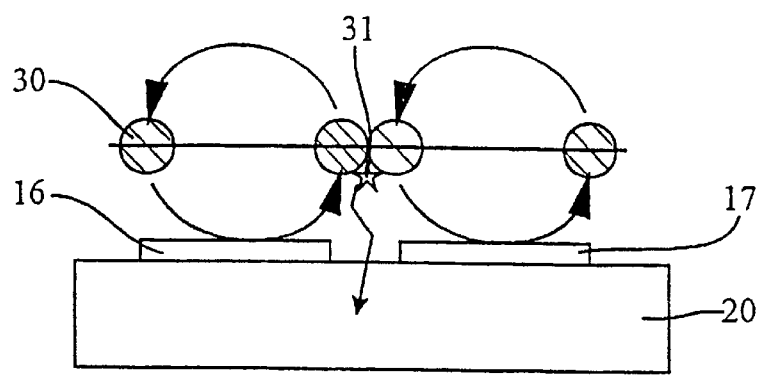

The present invention relates to electrochemoluminescent systems. It concerns, more particularly, a detector and a method for analyzing substances by generating and detecting the electrogenerated chemoluminescence (ECL) or electrochemoluminescence.

Chemoluminescence is used for analyzing biochemical or biological substances. It allows, in particular, traces of micro-organisms, hormones, viruses, antibodies, amines or proteins to be measured.

Chemoluminescent analysis consists in marking the substance sought by means of a chemoluminescent agent, the detection and analysis of which are achieved by measuring the light transmitted when, having been placed in an excited state, it returns to its initial state.

The excited state allowing light transmission is the product of a chemical reaction between two particular substances. The present invention concerns, more particularly, systems using an electrochemical reaction, called electrochemoluminescent systems, wherein at least one of the reagents is electrochemically produced from a substance initially present in the solution.

Known electrochemoluminescent systems generally include a cell for generating and detecting the electrogenerated chemoluminescence, which includes at least a working electrode, means for supplying the electrode with electric power, a photodiode for detecting the light generated and means for measuring the signal provided by the photodiode.

These systems use a single or two working electrodes, as will be described hereinafter. In both cases, in order to perform reliable measurements, the photodiode must be placed as close as possible to the place where the electrochemoluminescent reaction takes place. All the stray light must also be taken into account in order to eliminate as far as possible systematic errors.

Such conditions are relatively difficult to satisfy with respect to easy to use, inexpensive miniaturized systems.

In order to meet these requirements, the publication by Smith et al. "Electrochemiluminescence at microelectrodes for biosensing" (SPIE vol. 2978, 1977, pages 64–68, XP-002056761) discloses a miniaturized electrochemoluminescent cell whose different components are assembled to form a very compact structure.

The object of the present invention is to take an additional step in making electrochemoluminescent detectors of very small dimensions, which are simple and practical to use, are of low cost and allow a wide range of applications.

More precisely, the invention concerns an electrochemoluminescent detector for analyzing a biochemical or biological substance, of the type including at least one cell for generating and detecting the electrogenerated chemoluminescence, which includes:
  at least one working electrode made on a substrate;
  electric power supply means connected to said electrode;
  a photodiode for detecting the light generated by electrochemoluminescence; and
  means for measuring the signal provided by the photodiode.

According to the present invention, this detector is principally characterized in that the photodiode is produced by being integrated in the substrate of the working electrode.

In an advantageous manner, the cell includes two interdigitated working electrodes one of which is used as the anode and the other as the cathode. The cathode is made of carbon and the anode of a material selected from among platinum, gold, carbon and transparent metal oxides. The distance between the cathode and the anode is less than 10 microns.

According to a preferred embodiment, the cell includes a passivation layer in which the electrodes are integrated, while leaving a portion of their top surface in contact with the exterior, and an intermediate layer of dielectric material, arranged between the electrode and the substrate.

Preferably, the detector according to the invention includes two identical measuring cells, such as described above, whose respective electrodes are provided on the same substrate and whose respective photodiodes are made by being integrated in said substrate The electrode of only one of the cells is connected to the power supply means, and the measuring means include means for determining the difference between the signals provided by the photodiodes of the two cells. In this embodiment, the passivation layer and the intermediate layer are common to both cells.

The object of the present invention is also achieved by a method according to which the substance to be analyzed is in an aqueous solution. In this case, the cathode is made of carbon, while the anode is made of a material selected from among platinum, gold, carbon and other materials known to those skilled in the art, in particular transparent metal oxides, the distance between the cathode and the anode being less than 10 microns.

Figure 2:
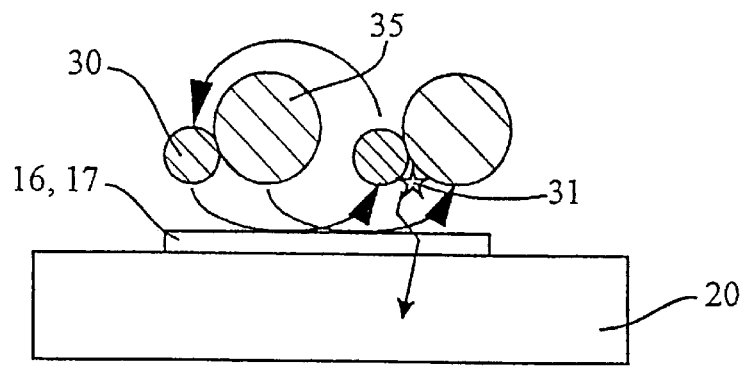
Figure 3:
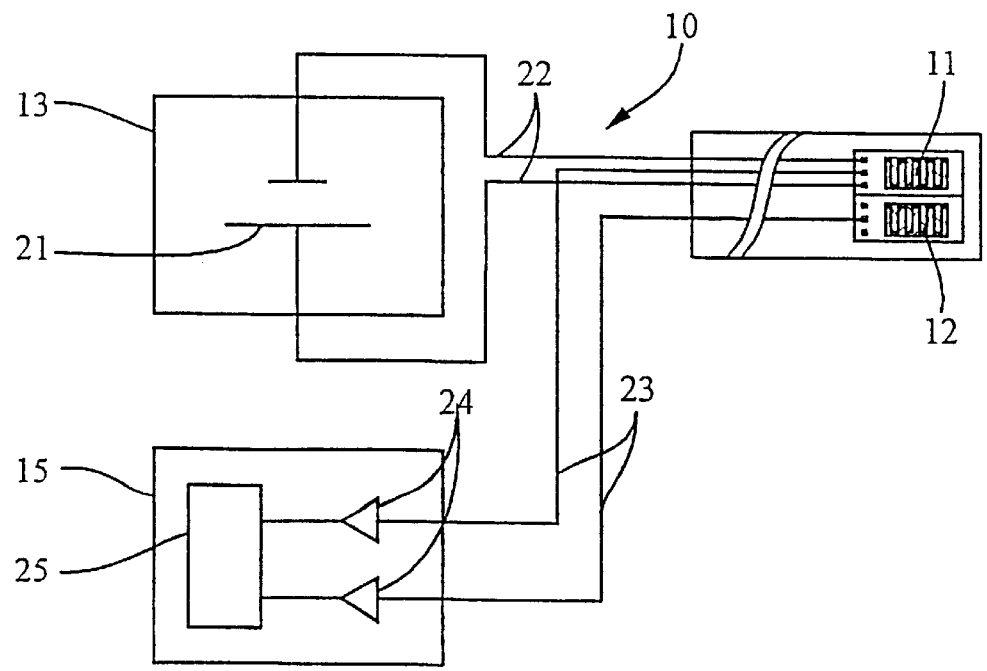
Figure 4:
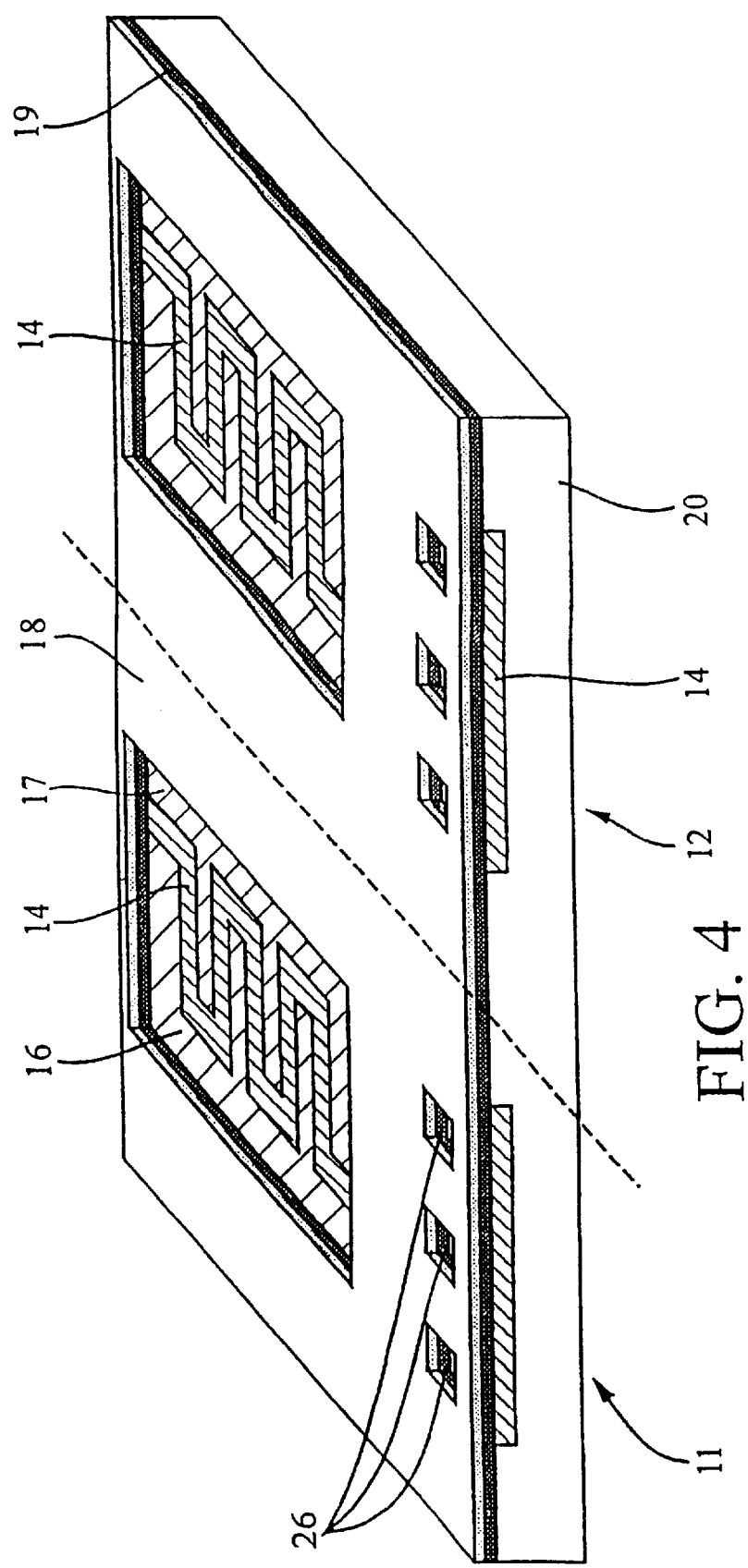

The present invention and the advantages thereof will be better understood with reference to the description of different embodiments and to the annexed drawings, in which:

FIG. 1 illustrates schematically an electrochemoluminescent reaction taking place on a cell with two working electrodes, FIG. 2 illustrates an electrochemoluminescent reaction taking place on a cell with only one working electrode, FIG. 3 is a schematic overall view of the detector according to the present invention, and FIG. 4 is a perspective view of a portion of the detector of FIG. 3.

As these Figures show, the electrochemoluminescent detector 10 according to the present invention essentially includes two identical measuring cells 11 and 12, whose same components are designated by the same reference numbers.

Each cell includes two working electrodes, an anode 16 and a cathode 17 which are separated by a distance of less than 10 microns, electric power supply means 13 for the electrodes of cell 11 only, a photoelectric detector 14 for detecting the light generated by electrochemoluminescence and means 15 for measuring the output signal of detector 14.

Cell 11 is the so called active cell, while cell 12 is the reference cell intended for measuring the background noise, which is why it is not supplied with electric power.

As FIG. 4 shows, anode 16 and cathode 17 are interdigitated. They are separated by a distance of less than 10 microns. In an advantageous manner, although this is not indispensable, these two electrodes are protected by a passivation layer 18 leaving a portion of their top surface in contact with the exterior. The whole assembly is deposited on an intermediate layer 19, which is itself arranged on an n type silicon substrate 20.

It is advantageous for electrodes 16 and 17 to be interdigitated, but other arrangements and geometries are possible provided that the distance separating them is less than 10 microns.

Passivation layer 18, intermediate layer 19 and substrate 20 are common to both cells.

Photoelectric detector 14 is formed of a photodiode made of an n type diffused zone in p type substrate 20, under interdigitated electrodes 16 and 17.

In other words, photodiode 14 is made by being integrated in substrate 20 on which interdigitated working electrodes 16 and 17 are deposited.

Intermediate layer 19 is formed dielectrically and assures galvanic insulation between electrodes 16 and 17 and photodiode 14. This layer is also used to assure protection of the cells from chemical attack by the surrounding environment. This allows the risk of deterioration of the cells to be minimized.

Another function of intermediate layer 19 is to reduce the reflection of light at the interface with substrate 20. This is achieved by adjusting the thickness and the refractive index of the layer as a function of the wavelength of the transmitted light, which depends on the product used as marker.

In a concrete use of the detector according to the invention, the marker is made of ruthenium (II) tris (2.2'-bipyridyl). Other products, such as luminol, may also be used.

Intermediate layer 19 is made of silicon nitride $Si_3N_4$ and has a thickness of approximately 0.4 microns, so as to minimize the reflections at 610 nm corresponding to the maximum wavelength transmission of ruthenium when the latter is used as a marker. This layer is advantageously deposited by a deposition method known by the name of "Plasma enhanced chemical vapor deposition" and by the abbreviation PECVD.

According to an advantageous embodiment, electrodes 16 and 17 are made of platinum, gold, carbon or transparent metal oxides known to those skilled in the art. In this case, they may be used to measure substances contained in organic solutions. They may also be used in detectors with a single working electrode, i.e. in which the two interdigitated electrodes are electrically connected to each other.

According to another embodiment, cathode 17 can be made of carbon, anode 16 being able to formed either of platinum, gold, carbon or transparent metal oxides. In this case, when the two electrodes are sufficiently close, namely at a distance of less then 10 microns, it is possible to perform an analysis of components in an exclusively aqueous solution or also in an organic solution Top passivation layer 18 allows the cells to be insulated from the surrounding environment, in order to minimize the risk of deterioration due to chemical attacks from such environment. This layer 18 can be made of a material such as silicon nitride $Si_3N_4$. Its thickness is approximately 0.4 microns and can also be deposited by the aforementioned "PECVD" method.

Power supply means 13 of active cell 11 include an electric power source 21 and conductive paths 22 made on a support, such as a printed circuit board, at the end of which the two cells are deposited. These conductive paths 22 connect electrodes 16 and 17 of active cell 11 to source 21. By way of example, the source supplies a triangular alternating voltage, at the speed of 100 mV/sec, varying from −1.45V to 1.65V to the cathode and a direct current voltage of 1.65V to the anode.

Measuring means 15 essentially include two conductive paths 23 made on the support of the two cells and connect the two photodiodes 14 to two amplifiers 24. These amplifiers receive the photocurrent generated by the photodiodes and supply an amplified signal to a measuring apparatus 25. The latter then determines a signal representative of the difference between the signal supplied by the photodetector of active cell 11 and that supplied by the photodetector of reference cell 12.

According to an advantageous embodiment, the electric connections 22 between electrodes 16 and 17 of active cell 11 and power source 21, and the electric connections 23 between the two photodiodes 14 and amplifiers 24 are achieved via connection zones 26 made at one end of the cells.

The operation of the detector of the present invention will now be described in the case, taken by way of example, in which it is sought to analyze a biochemical component, such as a protein. Ruthenium is then used as a marker. Determination thereof gives the determination of the biochemical component. In this case, two measuring methods are possible.

According to the first method of the invention, the two interdigitated working electrodes are used respectively as anode and cathode. More precisely, the protein to be analyzed, marked by ruthenium (II) tris (2.2'-bipyridyl), $Ru(bpy)_3^{2+}$, in aqueous solution, is introduced into a receptacle. The two cells 11 and 12 are then placed in the receptacle In active cell 11, the $Ru(bpy)_3^{2+}$ is reduced at cathode 17 to $Ru(bpy)_3^+$ and oxidizes into $Ru(bpy)_3^{3+}$ at anode 16. Following an annihilation reaction between $Ru(bpy)_3^+$ and the $Ru(bpy)_3^{3+}$, photons are released and detected by photodiode 14 of active cell 11. This reaction is illustrated in particular by FIG. 1.

The photocurrent generated by the release of the photons is amplified by amplifier 24 then sent to measuring apparatus 25.

Simultaneously, a parasitic photocurrent is generated in the two photodiodes 14. It is due to the light from the environment but also to the background noise of the cells themselves. This effect varies as a function of the temperature, which means that it is difficult to take into account by calculation.

The parasitic current affecting the measurement of active cell 11 is determined alone by photodiode 14 of reference cell 12 which is not powered. Of course, this is valid provided that both cells are subjected to the same conditions and that they have been made in the same manner.

Thus, by determining, in measuring apparatus 25, a difference between the signals from each of the two cells, a value corresponding to the current generated solely by electrochemoluminescence is obtained. The measurement is independent of stray light and variations in temperature. It is thus possible to perform measurements in ambient light, as well as in conditions in which the temperature varies.

According to the second method of the invention, the two interdigitated electrodes are used as a single working electrode. In practice, the cells are then the same as cells with two electrodes, with the only difference that the latter are simply connected to each other, either inside the cells or outside, for example, in the vicinity of the conductive paths.

In this case, the aqueous solution containing the ruthenium marked protein differs from that of the first method in that a co-reagent, such as an amine is used. An oxidation reaction of the amine and ruthenium is then induced by powering the anode. The chemical reaction between the oxidized amine and the $Ru(bpy)_3^{3+}$ generates the excited state of the ruthenium which generates the light detected by photodiode 14. This reaction in illustrated in particular by FIG. 2.

Measurement of the current supplied by photodiode 14 provides a measurement of the number of photons transmitted and, consequently, a measurement of the quantity of the marker, thus the substance to be analyzed.

The detector according to the invention, which has just been described, thus allows measurements to be performed simply with cells having one or two electrodes, according to the method selected.

A particularly important advantage of this detector lies in the fact that it integrates, in a same cell, electrodes 16 and 17 and photodiode 14. This makes the device particularly reliable and easy to use.

The presence of a subsidiary cell allows the influence of stray light and temperature variation to be easily eliminated, which allows the measuring conditions to be simplified and the reliability of the measurements to be significantly improved.

In the first method described, the proximity of the anode and the cathode and the use of a carbon cathode allows measurements to be performed in an exclusively aqueous solution, which is not possible with currently known devices Finally, it is to be noted that when photodiode 14 is biased in the blocked direction, the quantity of light is measured, whereas if it is biased in the conductive direction, the temperature is measured, which can prove advantageous in certain applications.

The present invention is not limited to the embodiments described. In particular, the materials used for the different layers and, most particularly intermediate layer 19 and passivation layer 18, must be adapted to the substances to be analyzed.

Likewise, the thickness of intermediate layer 19 must be adapted to the substance to be analyzed.

The device according to the present invention may be used to perform regular measurements in a receptacle, or for continuous measurements in which a flow of the substance to be analyzed moves with respect to the cell. This allows one to have a measurement of the evolution of the quantity of the substance to be analyzed, while eliminating the influence of temperature variations and modification in the stray light.

What is claimed is:

1. Electrochemoluminescent detector for analyzing a biochemical or biological substance, including at least one cell (11, 12) for generating and detecting the electrogenerated chemoluminescence, which includes:
   at least one working electrode (16, 17) made on a substrate (20);
   electric power supply means (13) connected to said electrode;
   a photodiode (14) for detecting the light generated by electrochemoluminescence; and
   means (15) for measuring the signal provided by the photodiode, characterized in that
   said photodiode (14) is produced by being integrated in said substrate (20).

2. Detector according to claim 1, characterized in that the cell includes two working electrodes, an anode (16) and a cathode (17).

3. Detector according to claim 2, characterized in that the two working electrodes (16, 17) are interdigitated.

4. Detector according to claim 2, characterized in that the cathode (17) is made of carbon, in that the anode (16) is made of a material selected from among platinum, gold, carbon and transparent metal oxides, and in that the distance between the cathode and the anode is less than 10 microns.

5. Detector according to claim 1, characterized in that the cell includes a passivation layer (18) in which said electrodes are integrated, while leaving a portion of their top surface in contact with the exterior.

6. Detector according to claim 1, characterized in that the cell includes an intermediate layer (19) made of a dielectric material, arranged between the electrode (16, 17) and the substrate (20).

7. Detector according to claim 6, characterized in that said intermediate layer (19) includes silicon nitride.

8. Detector according to claim 1, characterized in that it includes two identical measuring cells (11, 12) whose respective electrodes are made on the same substrate (20) and whose respective photodiodes (14) are made by being integrated in said substrate, in that the electrode of only one of the cells (11) is connected to the power supply means (13), and in that said measuring means (15) include means (25) for determining the difference between the signals provided by the photodiodes (14) of the two cells.

9. Detector according to claim 8, characterized in that the cell includes a passivation layer (18) in which said electrode is integrated, while leaving a portion of the electrode's top surface in contact with the exterior, and an intermediate layer (19) made of a dielectric material, arranged between the electrode (16, 17) and the substrate (20), and that the passivation layer (18) and the intermediate layer (19) are common to both cells.

10. Method for analyzing a biochemical biological substance by means of the detector
    according to claim 4, characterized by the steps:
    providing said substance in an aqueous solution,
    introducing said detector in said aqueous solution, and
    analyzing said aqueous solution by means of said detector.

11. Detector according to claim 3, characterized in that the cathode (17) is made of carbon, in that the anode (16) is made of a material selected from among platinum, gold, carbon and transparent metal oxides, and in that the distance between the cathode and the anode is less than 10 microns.

12. Detector according to claim 2, characterized in that the cell includes a passivation layer (18) in which said electrodes are integrated, while leaving a portion of their top surface in contact with the exterior.

13. Detector according to claim 3, characterized in that the cell includes a passivation layer (18) in which said electrodes are integrated, while leaving a portion of their top surface in contact with the exterior.

14. Detector according to claim 4, characterized in that the cell includes a passivation layer (18) in which said electrodes are integrated, while leaving a portion of their top surface in contact with the exterior.

15. Detector according to claim 2, characterized in that the cell includes an intermediate layer (19) made of a dielectric material, arranged between the electrodes (16, 17) and the substrate (20).

16. Detector according to claim 3, characterized in that the cell includes an intermediate layer (19) made of a dielectric material, arranged between the electrodes (16, 17) and the substrate (20).

17. Detector according to claim 4, characterized in that the cell includes an intermediate layer (19) made of a dielectric material, arranged between the electrodes (16, 17) and the substrate (20).

18. Detector according to claim 5, characterized in that the cell includes an intermediate layer (19) made of a dielectric material, arranged between the electrodes (16, 17) and the substrate (20).

19. Detector according to claim 2, characterized in that it includes two identical measuring cells (11, 12) whose respective electrodes are made on the same substrate (20) and whose respective photodiodes (14) are made by being integrated in said substrate, in that the electrode of only one of the cells (11) is connected to the power supply means (13), and in that said measuring means (15) include means (25) for determining the difference between the signals provided by the photodiodes (14) of the two cells.

20. Detector according to claim 3, characterized in that it includes two identical measuring cells (11, 12) whose respective electrodes are made on the same substrate (20) and whose respective photodiodes (14) are made by being integrated in said substrate, in that the electrode of only one of the cells (11) is connected to the power supply means (13), and in that said measuring means (15) include means (25) for determining the difference between the signals provided by the photodiodes (14) of the two cells.

* * * * *